US012746210B2

(12) United States Patent
Suk et al.

(10) Patent No.: US 12,746,210 B2
(45) Date of Patent: Sep. 29, 2026

(54) NANOSUSPENSION FORMULATION FOR TREATMENT OF PULMONARY FIBROSIS

(71) Applicants: The Johns Hopkins University, Baltimore, MD (US); Federal University of Rio De Janeiro, Universidade Federal do Rio de Janeiro (BR)

(72) Inventors: Jung Soo Suk, Clarksville, MD (US); Luisa Helena Andrade Da Silva, Rio de Janeiro (BR); Patricia Rocco, Rio de Janeiro (BR); Marcelo Morales, Rio de Janeiro (BR)

(73) Assignees: The Johns Hopkins University, Baltimore, MD (US); Federal University of Rio De Janeiro, Rio de Janeiro (BR)

( * ) Notice: Subject to any disclaimer, the term of this patent is extended or adjusted under 35 U.S.C. 154(b) by 220 days.

(21) Appl. No.: 18/415,202

(22) Filed: Jan. 17, 2024

(65) Prior Publication Data

US 2024/0285545 A1 Aug. 29, 2024

Related U.S. Application Data

(60) Provisional application No. 63/480,240, filed on Jan. 17, 2023.

(51) Int. Cl.

*A61P 11/00* (2006.01)
*A61K 9/00* (2006.01)
*A61K 9/51* (2006.01)
*A61K 31/496* (2006.01)

(52) U.S. Cl.

CPC .......... *A61K 9/5146* (2013.01); *A61K 9/0078* (2013.01); *A61K 9/5123* (2013.01); *A61K 31/496* (2013.01); *A61P 11/00* (2018.01)

(58) Field of Classification Search

CPC .. A61K 9/5146; A61K 9/0078; A61K 9/5123; A61K 9/0073; A61K 9/5153; A61K 31/506; A61P 11/00

See application file for complete search history.

(56) References Cited

U.S. PATENT DOCUMENTS

2019/0282565 A1* 9/2019 Liang ...................... A61P 11/00
2025/0268821 A1* 8/2025 Surber ................... A61K 47/24

OTHER PUBLICATIONS

Chen, et al., "Global and national burden and trends of mortality and disability . . . adjustelife years for silicosis, from 1990 to 2019: results from the Global Burden of Disease study 2019" Chen et al. BMC Pulmonary Medicine 22:240 (2022).
Duan, et al., "A Nanoparticle Delivery of Plasmid Encoding Hepatocyte Growth Factor for Gene Therapy of Silicosis in Mice" J Pharm Pharm Sci (www.cspsCanada.org) 24, 488-498, (2021).
Epstein-Shochet, et al., "Inhalation: A means to explore and optimize nintedanib's pharmacokinetic/pharmacodynamic relationship" Pulmonary Pharmacology & Therapeutics 63: 101933(2020).
Ghumman, et al., "Emerging drug delivery strategies for idiopathic pulmonary fibrosis treatment" European Journal of Pharmaceutics and Biopharmaceutics 164 1-12(2021).
Liu, et al., "Fullerene nanoparticles: a promising candidate for the alleviation of silicosis-associated pulmonary inflammation" Nanoscale, 12, 17470(2020).
Mangal, et al., "Pulmonary delivery of nanoparticle chemotherapy for the treatment of lung cancers: challenges and opportunities" Acta Pharmacologica Sinica 38: 782-797 (2017).
Rose, et al., "Silicosis" www.uptodate.com (2022).
Sauleda, et al., "Idiopathic Pulmonary Fibrosis: Epidemiology, Natural History, Phenotypes" Med. Sci., 6, 110(2018).
Silicosis—Level 4 cause, Global Health Metrics(2019).
Singer, et al., "Survival following lung transplantation for silicosis and other occupational lung diseases" Occupational Medicine 62:134-137(2012).
Xu, et al., "Co-delivery of bufalin and nintedanib via albumin sub-microspheres for synergistic cancer therapy" Journal of Controlled Release 338 705-718(2021).
Chen, et al., "Telmisartan Nanosuspension for Inhaled Therapy of COVID-19 Lung Disease and Other Respiratory Infection" Mol Pharm. 20(1): 750-757(2023).

* cited by examiner

*Primary Examiner* — Robert A Wax
*Assistant Examiner* — Ngoc-Anh Thi Nguyen
(74) *Attorney, Agent, or Firm* — PABST PATENT GROUP LLP

(57) ABSTRACT

An inhalable nanocrystal-based suspension formulation of nintedanib (NTB) (NTB-NS) possessing specific physicochemical properties to enhance drug retention in the lung was developed for localized treatment of pulmonary fibrosis via inhalation. This NTB-NS formulation was prepared using a wet-milling procedure in the presence of a surfactant, PLURONIC® F127, to endow the formulation with non-adhesive surface coatings to minimize interactions with therapy-inactivating delivery barriers in the lung.

20 Claims, 9 Drawing Sheets

Specification includes a Sequence Listing.

SEQUENCE LISTING

```
Sequence total quantity: 4
SEQ ID NO: 1          moltype = DNA  length = 20
FEATURE               Location/Qualifiers
source                1..20
                      mol_type = other DNA
                      organism = synthetic construct
SEQUENCE: 1
caacccagct ctggagaaac                                        20

SEQ ID NO: 2          moltype = DNA  length = 20
FEATURE               Location/Qualifiers
source                1..20
                      mol_type = other DNA
                      organism = synthetic construct
SEQUENCE: 2
gttctgagct ggcacagtga                                        20

SEQ ID NO: 3          moltype = DNA  length = 21
FEATURE               Location/Qualifiers
source                1..21
                      mol_type = other DNA
                      organism = synthetic construct
SEQUENCE: 3
ctaatggtgg accgcaacaa c                                      21

SEQ ID NO: 4          moltype = DNA  length = 20
FEATURE               Location/Qualifiers
source                1..20
                      mol_type = other DNA
                      organism = synthetic construct
SEQUENCE: 4
gacagccact caggcgtatc                                        20
```

NANOSUSPENSION FORMULATION FOR TREATMENT OF PULMONARY FIBROSIS

CROSS-REFERENCE TO RELATED APPLICATIONS

This application claims priority to and benefit of U.S. Ser. No. 63/480,240 filed Jan. 17, 2023, the teachings of which are incorporated herein.

STATEMENT REGARDING FEDERALLY SPONSORED RESEARCH

This invention was made with government support under grant HL136617 awarded by the National Institutes of Health. The government has certain rights in the invention.

FIELD OF THE INVENTION

This invention is generally in the field of pharmaceutical formulations for treatment of pulmonary fibrosis, including silicosis.

REFERENCE TO THE SEQUENCE LISTING

The Sequence Listing XML submitted as a file named "JHU_C_17526_US_ST26.xml" and having a size of 4,641 bytes is hereby incorporated by reference pursuant to 37 C.F.R. § 1.834(c)(1).

BACKGROUND OF THE INVENTION

Silicosis is an irreversible and progressive type of pulmonary fibrosis, that is caused by massive inhalation of crystalline silica dust at workplaces and affects millions of industrial workers worldwide. It is estimated that more than two million U.S. workers are under continuous exposure to silica at workplaces. Silica microparticles, upon deposition in the alveolar sacs, induce pro-inflammatory response, progressive fibrosis, and irreversible granuloma formation in the lung parenchyma, thereby gradually compromising the pulmonary function. As a result, this devastating disease presents high incapacitation rates, while there is no cure other than lung transplantation, a procedure with limited availability due to lack of suitable donor organs.

A tyrosine kinase inhibitor, nintedanib (NTB), has emerged as a potential silicosis treatment due to its inhibitory effects on key signaling pathways that promote silica-induced pulmonary fibrosis. The oral formulation of NTB is clinically used for treating other types of pulmonary fibrosis, including idiopathic pulmonary fibrosis (IPF) and chronic interstitial lung disease, to mitigate lung function decline and to minimize the risk of pulmonary exacerbation.

NTB is also under a phase II clinical trial to evaluate its therapeutic benefits in patients with occupational pneumoconiosis (NCT0461014). NTB acts by blocking the fibroblast growth factor receptor-1 and the platelet-derived growth factor receptor, thus disrupting downstream signaling cascades that promote proliferation of fibroblasts/myofibroblasts and collagen deposition. In addition, NTB inhibits Src pathway in silica-activated macrophages in vitro and in lung fibrosis in vivo and, in turn, thwarts the expression of fibrogenic mediators, such as transforming growth factor (TGF)-β. However, chronic and frequent use of the oral NTB formulation clinically approved for treating other fibrotic lung diseases often results in significant side effects.

SUMMARY OF THE INVENTION

An aerosolized, intratracheal or inhalable nanocrystal-based suspension formulation of nintedanib (NTB) (NTB-NS) possessing specific physicochemical properties to enhance drug retention in the lung was developed for localized treatment of pulmonary fibrosis via inhalation. This NTB-NS formulation was prepared using a wet-milling procedure in the presence of a surfactant, PLURONIC® F127, to endow the formulation with non-adhesive surface coatings to minimize interactions with therapy-inactivating delivery barriers in the lung.

It was found that NTB-NS, following intratracheal administration, provided robust anti-fibrotic effects and mechanical lung function recovery in a silica-induced pulmonary fibrosis model, whereas a 100-fold greater oral NTB dose given with a triple the dosing frequency failed to do so. Importantly, several key pathological phenotypes were fully normalized by NTB-NS without displaying notable local or systemic adverse effects, evidencing that the localized treatment of silicosis and other fibrotic lung diseases using formulations of this type is effective.

BRIEF DESCRIPTION OF THE DRAWINGS

FIG. 1A is a graph of particle size (i.e., hydrodynamic diameter, nm) as a function of PLURONIC® F127 concentration. NTB was dispersed in F127 solutions at varying concentrations (%). Data represents average and standard deviation of particle size from three independent samples, measured in triplicate. Differences are statistically significant compared to (†) 1% F127 and (‡) 2% F127 ($p<0.05$; one-way ANOVA followed by a Tukey post-hoc test). FIG. 1B is a graph of particle size (i.e., hydrodynamic diameter, nm) as a function of NTB concentration (mg/ml). NTB was suspended at varying concentrations in 1% F127 solution. Data represents average and standard deviation of particle size from three independent samples, measured in triplicate. Differences are statistically significant compared to (†) 5 mg/mL NTB and (‡) 15 mg/mL NTB ($p<0.05$; one-way ANOVA followed by a Tukey post-hoc test).

FIG. 3A is a graph of the distribution of hydrodynamic diameters (nm) of NTB-NS. FIG. 3B is X-ray diffraction crystallography of NTB-NS. FIG. 3C is a graph of the colloidal stability of NTB-NS in water (gray circles) and in mouse bronchoalveolar lavage fluid (BALF, black squares), a physiologically relevant lung environment, measured as hydrodynamic diameter (nm) over time (hrs). Data represents mean±SD (n=3 independent samples).

FIG. 8A is a graph quantifying collagen deposition in alveolar septa of the lung parenchyma (n=6 mice per group except 0.1 mg/kg NTB-NS group). Scale bars=100 μm. FIGS. 8B and 8C, respectively, quantify the fractional area occupied by granulomas in the lung tissue (FIG. 8B) and of collagen deposition in granulomas (FIG. 8C) (n=6 mice per group except 0.1 mg/kg NTB-NS group). Bars represent mean±SD. The differences are statistically significant as indicated (*p<0.05, p<0.01, *p<0.001; one-way ANOVA followed by a Tukey post-hoc test).

(FIG. 10A, FIG. 10B) PK of intratracheally administered telmisartan NS (TEL-NS; 0.1 mg/kg) versus identically administered telmisartan free-drug (TEL-FD; 0.1 mg/kg) or orally administered TEL-FD (1 mg/kg; i.e., 10-times greater dose). (FIG. 10C) Lung PK of intratracheally administered TEL-NS prepared with POLYSORBATE® 80 (T80/TEL-NS) versus PLURONIC® F127 (F127/TEL-NS). *p<0.05; p<0.01; **p<0.001.

DETAILED DESCRIPTION OF THE INVENTION

I. Definitions

Figure 1A:
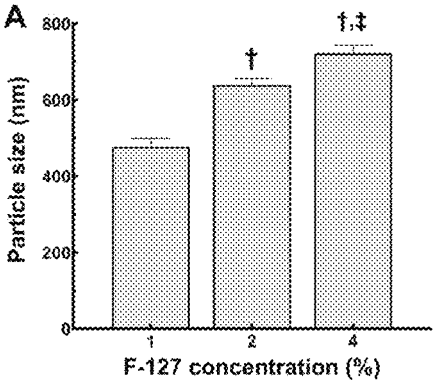
FIGS. 1A and 1B are graphs of the optimization and characterization of NTB-NS formulations.

The term "nanosuspension" of an active agent refers to a nanoparticulate form of the agent, typically a synthetic or natural compound having a molecular weight of less than 2000 Da, more typically less than 1500 or 1000 Da, having dimensions between about 1 nm and less than about 1 micron, inclusive, which is suspended in a pharmaceutically acceptable carrier effective for the route of administration. Nanosuspensions typically are submicron colloidal dispersions of nanosized drug particles stabilized by surfactants.

An "aerosolized" formulation is one in which the agent to be delivered is in the form of a fine spray or colloidal suspension in the air. This may be pure agent or agent in combination with excipient or carrier, which will typically be a liquid such as sterile water and saline if the drug is in the form of a nanosuspension.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Surfactant is a general name for substances that absorb to surfaces or interfaces to reduce surface or interfacial tension. These agents aid wetting and dispersion of hydrophobic active pharmaceutical ingredients, and they usually act by reducing the interfacial tension between solids and liquids in suspensions.

"Excipient" is used herein to include a pharmaceutically acceptable compound that is not a therapeutically or biologically active compound. An excipient should generally be inert and non-toxic to the subject.

The terms "biocompatible" and "biologically compatible" generally refer to materials that are, along with any metabolites or degradation products thereof, generally non-toxic to the recipient, and do not cause any significant adverse effects to the recipient. Generally speaking, biocompatible materials are materials which do not elicit a significant inflammatory, immune or toxic response when administered to an individual.

The terms "reduce", "inhibit", "alleviate" or "decrease" are used relative to a control, either no other treatment or treatment with a known degree of efficacy. One of skill in the art would readily identify the appropriate control to use for each experiment. For example, a decreased response in a subject or cell treated with a compound is compared to a response in subject or cell that is not treated with the compound.

The terms "treating" or "preventing" mean to ameliorate, reduce or otherwise stop a disease, disorder or condition from occurring or progressing in an animal which may be predisposed to the disease, disorder and/or condition but has not yet been diagnosed as having it; inhibiting the disease, disorder or condition, e.g., impeding its progress; and relieving the disease, disorder, or condition, e.g., causing regression of the disease, disorder and/or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain. Desirable effects of treatment include decreasing the rate of disease progression, ameliorating or palliating the disease state, and remission or improved prognosis. For example, an individual is successfully "treated" if one or more symptoms associated a disease or disorder of the eye is mitigated or eliminated.

The term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease or disorder, and the treatment being administered. The effect of the effective amount can be relative to a control.

The term "analog" refers to a chemical compound with a structure similar to that of another "reference" compound, but differing from it in respect to a particular component, functional group, atom, etc.

The term "derivative" refers to a compound, which is formed from a parent compound by one or more chemical reaction(s).

II. Formulations

A. Therapeutic or Prophylatic Agents

Currently, two drugs are FDA-approved for treatment of idiopathic pulmonary fibrosis (IPF), which is the most common form of PF. These include nintedanib (OFEV® and VARGATEF®) and pirfenidone (ESBRIET®). These medications are called anti-fibrotic agents, meaning that they have shown in clinical trials to slow down the rate of fibrosis or scarring in the lungs. These drugs are approved for patients with mild, moderate, and severe IPF.

Nintedanib is an oral tryosine kinase inhibitor used for the treatment of idiopathic pulmonary fibrosis and along with other medications for some types of non-small-cell lung cancer.

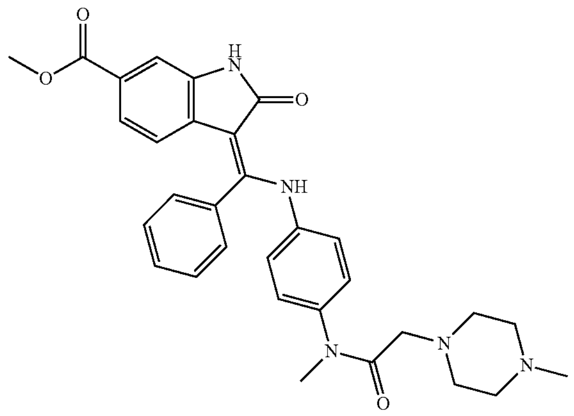

In March 2020, it was approved for use in the United States to treat chronic fibrosing (scarring) interstitial lung diseases (ILD) with a progressive phenotype (trait). It is the first treatment for this group of fibrosing lung diseases that worsen over time that was approved by the U.S. Food and Drug Administration (FDA).

Common side effects include abdominal pain, vomiting, and diarrhea. Nintedanib is used to treat idiopathic pulmonary fibrosis (IPF; scarring of the lungs with an unknown cause). It is also used to treat certain types of chronic fibrosing interstitial lung diseases (ILD; an ongoing disease in which there is increased scarring of the lungs). Nintedanib is also used to slow the rate of decline in lung function in people with systemic sclerosis-associated interstitial lung disease (SSc-ILD; also known as scleroderma-associated ILD: a disease in which there is scarring of the lungs that is often fatal). It is a small molecule tyrosine-kinase inhibitor, targeting vascular endothelial growth factor receptor, fibroblast growth factor receptor and platelet derived growth factor receptor.

Other anti-fibrotic kinase inhibitors could also be used.

B. Surfactants

There are several general classes of surfactants used in pharmaceutical suspensions, including anionic surfactants, cationic surfactants, amphoteric surfactants, and non-ionic surfactants. Non-ionic surfactants are the largest group of surfactants used in the formulation of pharmaceutical suspensions. These surfactants are nonelectrolytes; that is, their hydrophilic groups do not ionize at any pH value. There are several different types of nonionic surfactants available. Since many of the surfactants in this group are esters, they are usually susceptible to hydrolysis under conditions of high or very low pH. The final choice of non-ionic surfactant depends on a variety of factors, but chief among them is the Hydrophilic-lipophilic balance (HLB) value and their chemical compatibility with other components of the formulation. Examples of substances under this group of surfactants are Polyoxyethylene sorbitan fatty acid esters (Polysorbate, POLYSORBATE®), Polyoxyethylene 15 hydroxy stearate (MACROGOL 15 hydroxy stearate, SOLUTOL HS15®), Polyoxyethylene castor oil derivatives (CREMOPHOR® EL, ELP, RH 40), Polyoxyethylene stearates (MYRJ®), Sorbitan fatty acid esters (SPAN®), Polyoxyethylene alkyl ethers (BRIJ®), and Polyoxyethylene nonylphenol ether (NONOXYNOL®). Preferred sufactants are those approved by the Food and Drug Administration for pulmonary or respiratory use, such as polysorbate 80.

In the preferred embodiment, the surfactant is PLURONIC F127, a triblock copolymer composed of a central hydrophobic chain of poly(propylene oxide) (70 units) flanked by two hydrophilic chains of poly(ethylene oxide) (20 units each), also referred to as a nonionic polyoxyethylene-polyoxypropylene block co-polymer with the general formula $HO(C_2H_4O)a(—C_3H_6O)b(C_2H_4O)a$. It is available in different grades which vary from liquids to solids. It is used as an emulsifying agent, solubilizing agent, surfactant, and wetting agent for antibiotics. Poloxamer is also used in ointment and suppository bases and as a tablet binder or coater.

C. Cryoprotectant

When the formulation is lyophilized for storage in dry form, the formulation may include a lyoprotectant, such as a disaccharide-based lyoprotectant like sucrose or trehalose.

In a preferred embodiment, the formulation is lyophilized with between about 0.1 and 10% lyoprotectant, preferably about 3% by weight, most preferably about 3% sucrose.

III. Methods of Making Nanocrystal Formulations

The formulations are prepared using standard techniques, as exemplified below. Nearly 90% of newly discovered drugs are poorly water-soluble, a factor that limits their biological application, and poses a challenge to their pharmaceutical development. Nanocrystals improve the aqueous solubility of drugs, therefore enhancing their bioavailability. Briefly, the surface area of drug particles increases by downsizing them to the nanometer range, facilitating their dissolution and then enhancing their solubility.

The reduction of particle size can be achieved by "top-down" approaches, which are based on mechanically generated shear that breaks the drug into nanoparticles. Top-down approaches include homogenization and wet milling. In the first method, size reduction is achieved by passing the suspension through a small aperture under a high pressure, generating strong collision forces that break drug microparticles to nano-size range. In wet milling, the drug is initially dispersed in an aqueous surfactant solution and then crushed by milling beads under high mechanical force. Surfactant can also be applied by spraying onto the nanoparticles.

Top-down approaches are cost-effective, highly scalable, and not require the use of organic solvents, being widely used for development of new formulations. Drug nanocrystals can also be generated by "Bottom-up" approaches, based on precipitation and evaporation techniques that enable to controlled crystal growth from solutions. Precipitation of drug nanoparticles can be achieved in response to antisolvents, to acid-base reactions and to high gravity environments. Nanosuspensions can also be generated by the emulsion-solvent evaporation technique, that consists of drug dissolution in an organic solvent, emulsification into an aqueous phase, and rapid evaporation of the organic phase under low pressure.

IV. Methods of Use

A. Disorders to be Treated

There are five main categories of pulmonary fibrosis that have identifiable causes. In most cases, they are drug-induced, radiation-induced, environmental, autoimmune, or occupational. However, pulmonary fibrosis may also arise from unknown causes. In the United States, environmental and autoimmune causes seem to be the most common types of PF of known cause. Some medications can cause PF. Drugs used to treat cancer (chemotherapy), drugs used to treat abnormal heart rhythms (such as amiodarone), drugs used to treat inflammatory conditions (such as methotrexate), and an antibiotic used to treat urinary tract infections (nitrofurantoin) are some of the better-known drugs that can cause injury, inflammation, and scarring in the lungs. Numerous other drugs have been implicated as causes of PF in some cases.

Radiation to the chest for lymphoma; Hodgkin's disease; or breast, lung, and other cancers; can also injure the lung and cause fibrosis. Inhaled environmental substances can cause a form of PF called hypersensitivity pneumonitis (HP) or chronic hypersensitivity pneumonitis. HP occurs when the lungs react with inflammation and scarring after breathing in substances such as mold spores, bacteria, animal proteins (especially from indoor or caged birds), or other known triggers.

Substances found in occupational settings can cause a form of PF called pneumoconiosis. Exposure to inorganic dusts including asbestos, silica, coal dust, beryllium, and hard metal dusts can cause lung injury when they are inhaled on a regular basis, and for a significant period of time. Autoimmune diseases are also called connective tissue diseases, collagen vascular diseases, or rheumatologic diseases. "Auto" means self and "immune" refers to the immune system. If you have an autoimmune disease that affects your lungs, it means that your body's immune system is attacking your lungs. Examples of autoimmune diseases that can cause PF include: Rheumatoid arthritis; Scleroderma (also called systemic sclerosis); Sjögren's syndrome; and Polymyositis, dermatomyositis, and antisynthetase syndrome.

Idiopathic pulmonary fibrosis (IPF) is scarring of the lung where the cause is not known. To make a diagnosis, your doctor will take a thorough history to try to identify potential exposures, causes of injury, or other diseases that might have led to scarring of the lung. If a cause is found, then your diagnosis would not be IPF. The doctor will use detailed X-rays called high-resolution computed tomography (HRCT) and sometimes a lung biopsy to look at the scarring. IPF typically has a distinctive scarring pattern called usual interstitial pneumonia (UIP). A diagnosis of IPF requires that a doctor cannot find a cause for your lung scarring, and that the UIP scarring pattern is seen on your HRCT or surgical lung biopsy sample.

Although IPF is considered to be a disease of unknown cause, we do know some factors that increase the risk of getting IPF, including aging (IPF is rare before age 50), cigarette smoking, and having certain genetic predispositions.

B. Methods of Administration

The formulations are administered by aerosolization (i.e., nebulization), inhalation, or intratracheal instillation.

The dosage is based on the approved oral formulation with the knowledge that the dosage by this route of administration is less, typically 10 to 100 times less, as demonstrated in the example, although specific dosage ranges can be calculated using standard dose ranging, by one of skill in the art.

In a preferred embodiment, the final product will be a lyophilized nanosuspension dry powder co-packaged with a medical-grade vehicle solution (e.g., water, hypotonic or isotonic saline). The powder can be solubilized in the medical-grade vehicle solution and self-dosed by patients via a portal nebulizer. As described here, the dose would be markedly lower than the clinically used oral dose, as confirmed by clinical pharmacokinetics study.

EXAMPLES

Example 1: Formulation and Characterization of NTB-NS

Materials and Methods

Nintedanib (NTB) in a free-base form presents low aqueous solubility, which reduces its bioavailability in the physiological lung environment. A formulation that could be stably dispersed in aqueous solutions to be directly administered into the lung was developed by engineering a nanocrystal-based NS formulation of NTB (i.e., NTB-NS) by varying the variables to yield particles with non-adhesive surface coatings and nanoscale dimensions to potentially minimize mucus entrapment and macrophage uptake, following inhaled administration. The ability to do so increases the therapeutically available drug concentration in the lung.

Preparation and Characterization of NTB-NS

NTB in a free-base form (LC Laboratories; Woburn, USA) was dispersed in an aqueous PLURONIC® F127 (Sigma-Aldrich, St. Louis, USA) solution at varying NTB and F127 concentrations. This dispersion was then transferred to a tube containing 1.5 g of yttria-stabilized 0.5 mm zirconium oxide beads (Next Advance, Inc.; Troy, USA), and wet bead-milling was performed using a TISSUE LYSER LT® (Qiagen Inc, Germantown, MD), at a speed of 3000 oscillations/minute for 10 hours.

Wet milling was performed at 4° C. to dissipate heat. Subsequently, NTB-NS was washed with ultrapure water to remove free NTB and/or F127. All preparation steps were performed using aseptic technique.

Physicochemical properties of NTB-NS, including particle hydrodynamic diameter, polydispersity index (PDI), and surface charge (i.e., ζ-potential), were measured using a Zetasizer Nano ZS (Malvern Panalytical; Malvern, United Kingdom) at 90° scattering angle. Hydrodynamic diameter/PDI and ζ-potential were measured in ultrapure water and 10 mM NaCl, respectively. The colloidal stability of the formulation was confirmed by monitoring the change of the hydrodynamic diameters of NTB-NS in ultrapure water or in BALF every 20 minutes up to 6 hours at 37° C.

To determine the impact of aerosolization on the formulation, NTB-NS was diluted in saline at 0.02% w/v and aerosolized by a vibrating mesh nebulizer (Aerogen Solo, Chicago, IL) controlled by an Analog Discovery 2 data acquisition device (Digilent, Pullman, WA). Fresh or nebulized NTB-NS was deposited onto an electron microscope grid (EMS Sciences, Hatfield, PA), and particle size and morphology before and after nebulization were evaluated by transmission electron microscopy (Hitachi H7600, Hitachi, Ltd; Tokyo, Japan).

Solid-state characterization was performed using a LabX XRD-6100 X-ray Diffractometer (Shimadzu Corp, Kyoto, Japan), operated with 40 kV power and 30 mA current. X-ray powder diffraction patterns were determined from 3° to 45° on the two theta (2θ) scale, at a step size of 20° per second. Encapsulation efficiency was determined by LC-MS/MS. Briefly, NTB-NS was fully dissolved in acetonitrile/methanol (2:1, v/v), transferred to autosampler vials and run through the HPLC (Prominence-i LC-2030, Shimadzu), equipped with a PHENOMENEX LUNA®, C18 (4.6×150 mm, 5 μm) column, at room temperature.

The water/acetonitrile/trifluoroacetic acid mobile phase (35: 65:0.1, v/v) was run at isocratic mode for a total of 10 minutes. The column effluent was monitored using a mass-spectrometric detector (SCIEX TRIPLE QUADRAPOLE™ 5500 SCIEX, Vaughan, Canada) with electrospray ionization operating in positive mode. For the sterility assessment, NTB-NS or F127 solution was applied onto the plate with tryptic soy agar growth medium (Fluka Analytical, St Louis, MO, USA), followed by a one-week incubation at 37° C. and evaluation of colony formation. Ultrapure water and a suspension of *Pseudomonas aeruginosa* 01 (ATCC 27853, $5\times10^7$ CFU in 200 μL saline) served as negative and positive controls, respectively.

To assess the effect of lyophilization-rehydration on the particle colloidal stability, freshly prepared NTB-NS was lyophilized in the presence or absence of either sucrose or trehalose at a final concentration of 3%. After a 48-hour freeze-drying process, NTB-NS was rehydrated in ultrapure water and analyzed for physicochemical properties using a Zetasizer Nano ZS (Malvern).

Results

Figure 1B:
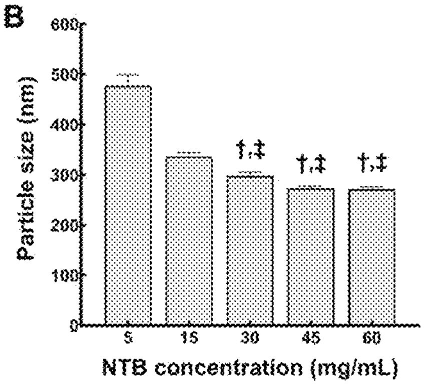

The results of the optimization and characterization of the NTB-NS formulation are shown in FIGS. 1A and 1B. FIG. 1A shows particle size (i.e., hydrodynamic diameter) as a function of F-127 concentrations. Data represents average and standard deviation of particle size from three independent samples, measured in triplicate. Differences are statistically significant compared to (†) 1% F127 and (‡) 2% F127 (P<0.05; one-way ANOVA followed by a Tukey post hoc test). FIG. 1B shows particle size as function of NTB concentration. NTB was suspended at varying concentrations in 1% F127 solution. Data represents average and standard deviation of particle size from three independent samples, measured in triplicate. Differences are statistically significant compared to (†) 5 mg/mL NTB and (‡) 15 mg/mL NTB (P<0.05; one-way ANOVA followed by a Tukey post hoc test).

Microbiological analysis of NTB-NS showed no colonies were observed on tryptic soy agar culture dishes, 7 days after inoculation with water, 1% F127, or NTB-NS, similar to the negative control group but in contrast to the positive control with bacterial culture.

Figure 2:
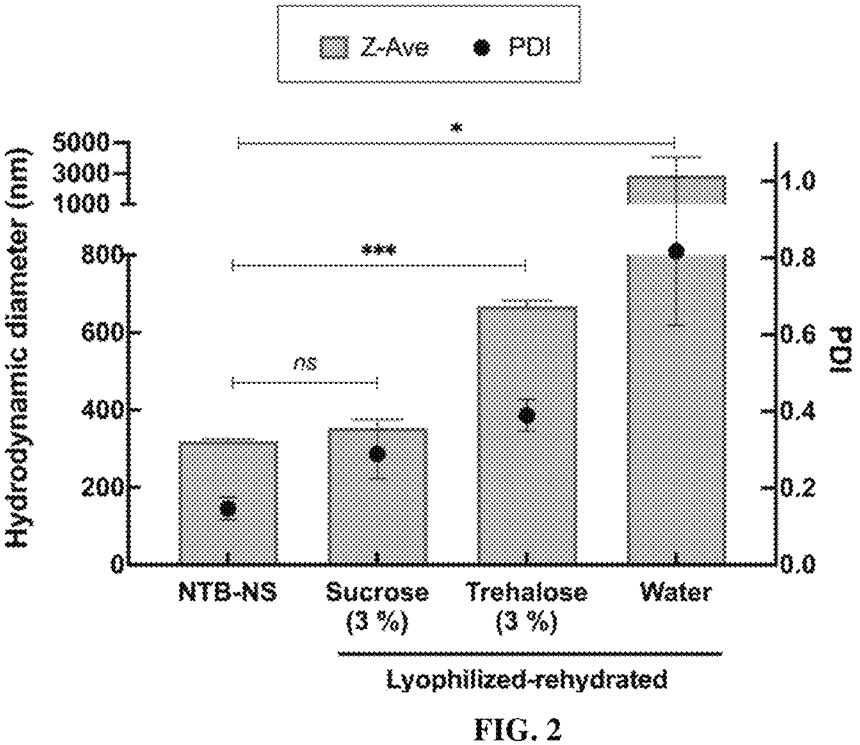
FIG. 2 is a graph of the effect of lyophilization on the physicochemical properties of NTB-NS. Hydrodynamic diameters (bars, nm) and PDI values (dots) measured before and after lyophilization-rehydration of NTB-NS in presence of a disaccharide-based lyoprotectant, either sucrose or trehalose, or without any lyoprotectant (Water). Data represents mean±SD (n=5 independent samples). The differences in hydrodynamic diameters are statistically significant as indicated (*$p<0.05$, ***$p<0.001$; one-way ANOVA followed by a Tukey post-hoc test).

FIG. 2 shows the effect of lyophilization on the physicochemical properties of NTB-NS. Hydrodynamic diameters (bars) and PDI values (dots) measured before and after lyophilization-rehydration of NTB-NS in presence of a disaccharide-based lyoprotectant, either sucrose or trehalose, or without any lyoprotectant (Water). Data represents mean±SD (n=5 independent samples). The differences in hydrodynamic diameters are statistically significant as indicated (*P<0.05, *** P<0.001; one-way ANOVA followed by a Tukey post hoc test). Sucrose at 3% maintained the hydrodynamic diameter close to pre-lyophilization.

For long-term storage as a powder form, NTB-NS was lyophilized in presence or absence of a disaccharide-based lyoprotectant, and subsequently, the lyophilized NTB-NS was rehydrated for physicochemical characterization. It was found that lyophilization in 3% sucrose did not perturb the particle size whereas significant aggregation was observed when NTB-NS was lyophilized in 3% trehalose or without any lyoprotectant (FIG. 2).

The concentration ranges of poloxamer 407 (i.e., PLURONIC® F127) and NTB were tested, where F127 endows the formulation with non-adhesive surface coating via physical adsorption, and determined a formulation prepared at 1% F127 and 45 mg/mL NTB to be the best formulation. The NTB-NS exhibited polygonal structure and hydrodynamic diameters of 333.3±9.5 nm with polydispersity indices of 0.21±0.02 (Table 1).

TABLE 1

Physicochemical characterization of NTB-NS.

| Hydrodynamic diameter (Z-Ave) [nm] | Polydispersity index | ζ-potential [mV] | Encapsulation efficiency [%] |
|---|---|---|---|
| 333.3 ± 9.5 | 0.21 ± 0.02 | 8.1 ± 0.5 | 89.5 ± 2.2 |

Data represents mean ± SD (n = 3 independent samples).

It was found that approximately 90% of the initial NTB amount was loaded into the final NS formulation (Table 1), which was markedly greater than encapsulation efficiencies of NTB enabled by other commonly used delivery platforms, such as liposomes (34%) and polymeric nanoparticles (5%).

Figure 3A:
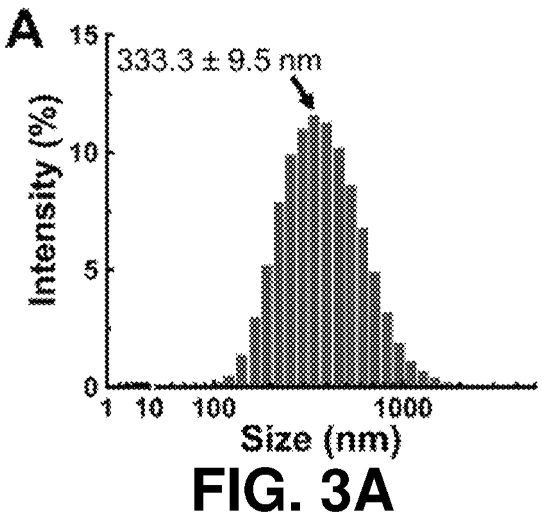
FIGS. 3A-3C are graphs of the physicochemical properties of NTB-NS.
Figure 3B:
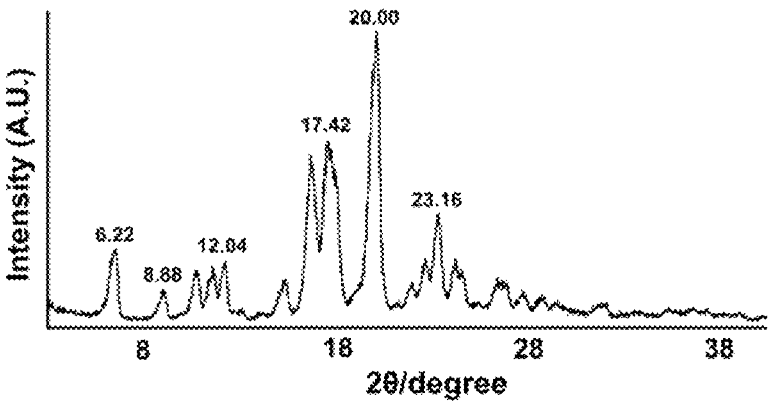
Figure 3C:
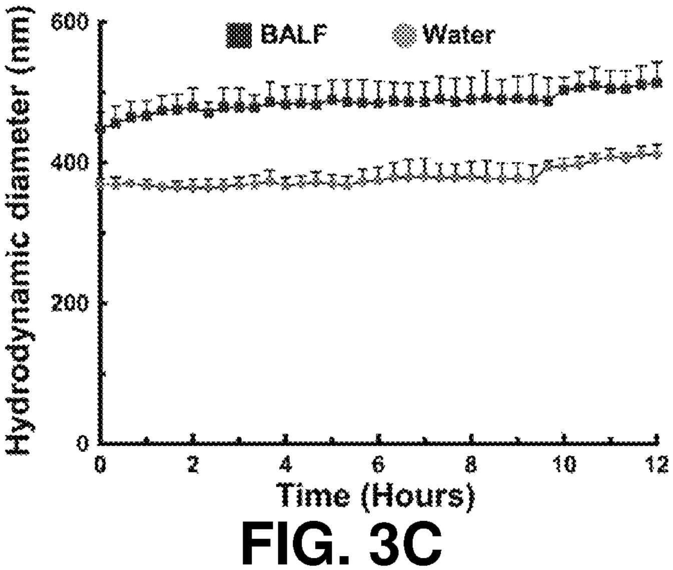
Figure 4A:
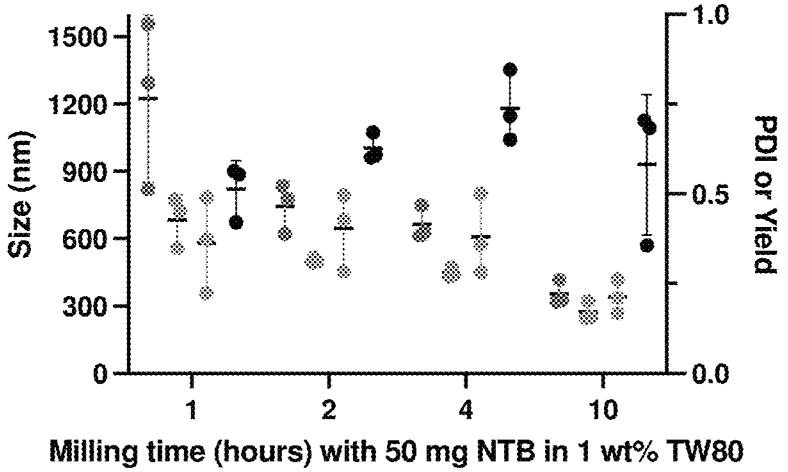
FIG. 4A is a graph of the effect of milling time (hours) of 50 mg NTP in 1 wt % TW80 on size (nm) and PDI or yield.
Figure 4B:
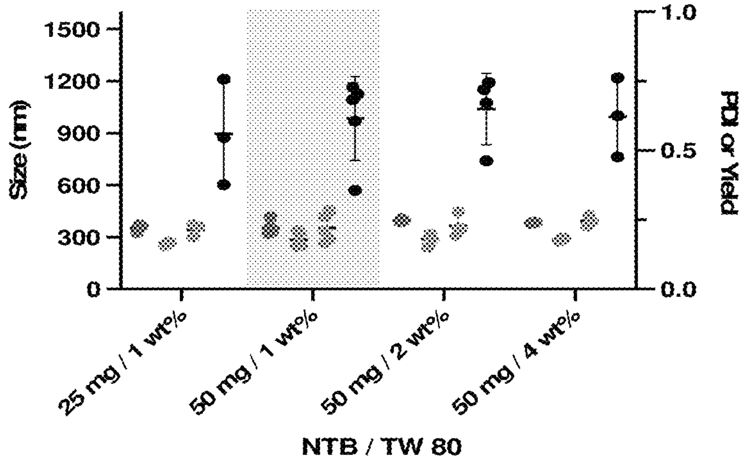
FIG. 4B is a graph of the effect of concentration (mg/1, 2 or 4 wt %) on size (nm) and PDI or yield.
Figure 4C:
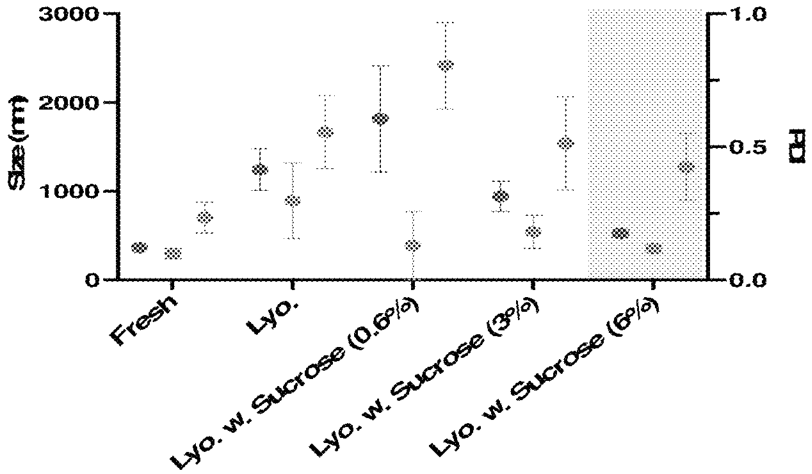
FIG. 4C is a graph of the effect of sucrose concentration (0, 0.6, 3, and 6%) of lyophilized drug, compared to fresh and lyophilized with no sucrose.
Figure 4D:
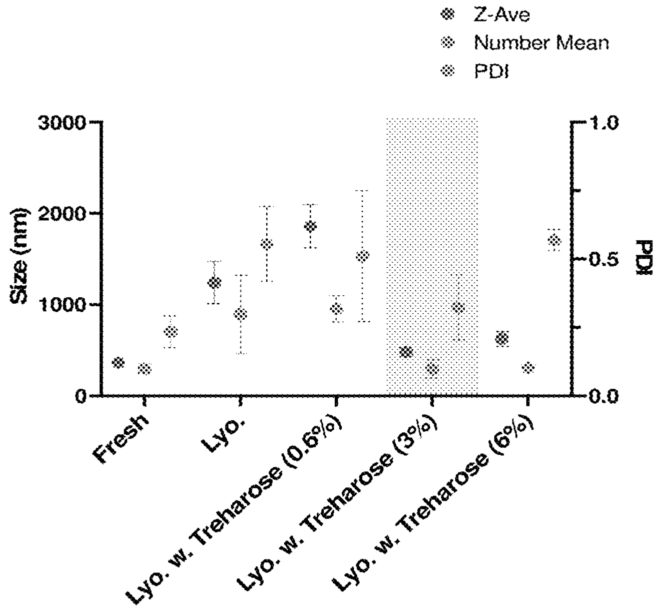
FIG. 4D is a graph of the effect of treharose concentration (0, 0.6, 3, and 6%) of lyophilized drug, compared to fresh and lyophilized with no treharose.
Figure 5A:
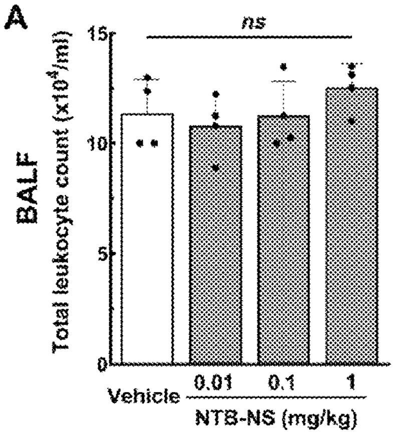
FIGS. 5A and 5B are graphs of the total leukocyte counts (5A) and percentage of neutrophils (5B) in BALF for 0, 0.01, 0.1, and 1 mg/kg NTB-NS, 24 hours after NTP-NS administration.
Figure 5B:
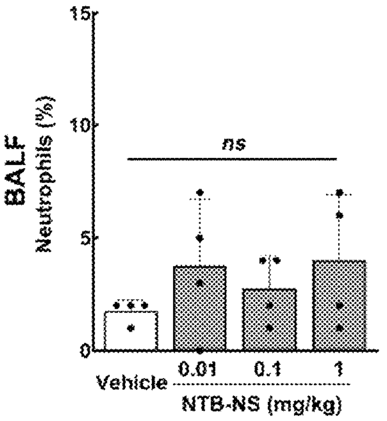
Figure 5C:
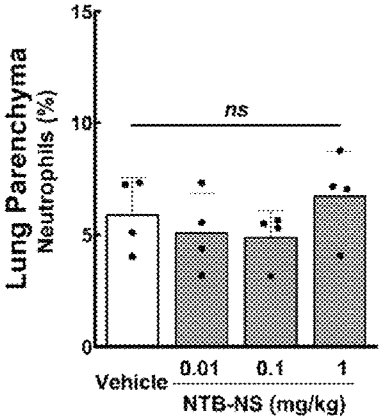
FIG. 5C is a graph of the percentage of neutrophils in lung parenchyma. Bars represent mean±SD (n=4 mice per group). The differences are not statistically significant as indicated (ns; one-way ANOVA followed by a Tukey post-hoc test).

The size (FIG. 3A) and morphology of NTB-NS retained after being aerosolized via a vibrating mesh nebulizer, were then confirmed via transmission electron microscopy. X-ray diffraction analysis revealed that NTB-NS existed as crystalline solids with refraction angles (20 scale) of 6.22°, 8.88°, 12.04°, 17.42°, 20° and 23.16° (FIG. 3B). Unlike in water, hydrodynamic diameters of NTB-NS slightly increased immediately upon incubation in bronchoalveolar lavage fluid (BALF) at 37° C. but the particle size remained unchanged at least up to 12 hours (FIG. 3C), underscoring excellent colloidal stability in a physiologically relevant lung environment. NTB-NS was prepared using aseptic technique, autoclaved utensils, and sterile-filtered solutions inside a laminar flow hood to avoid bacterial contamination, etc., and the sterility was confirmed by the absence of microbial colonies following a one-week inoculation on tryptic soy agar plates.

Example 2: Effect of Sucrose and Trehalose on Particle Physiochemical Properties Materials and Methods Particles were mixed with excipients known to be cryoprotectants, specifically sucrose and treharose, and their effect on the particle physiochemical properties compared over time for the effect on particle stability. This study is based on a NTB nanosuspension formulation with "polysorbate 80" as a surface stabilizer (while the other figures are based on a formulation with "Pluronic F127" as a surface stabilizer.

The effect on particle size, zeta potential and PDI was determined, comparing fresh, lyophilized, lyophilized with 0.6%, 3% or 6% sucrose or 0.6%, 3% or 6% treharose.

Results

The effects of adding sucrose or treharose to particles as a function of concentration over times were determined. The results are shown in FIG. 4A-4D. Lyophilization causes a doubling in particle size measured as number mean, and an even greater increase on Z-average and PDI. These changes are minimized by addition of 0.6 to 6% sucrose or trehalose.

Example 3: In Vivo Safety of Locally Administered NTB-NS in the Lungs of Healthy Animals Materials and Methods To evaluate preclinical safety, healthy C57BL/6 mice were dosed with NTB-NS via intratracheal instillation to ensure reliable dose-response assessment, since a fraction of nebulized drugs is deposited in the oropharynx during the transit to the deeper lung. NTB-NS doses were selected to be tested by benchmarking prior studies demonstrating that oral administration of 100 mg/kg NTB rendered approximately 2.5 μg of the drug available in mouse lungs, which roughly correspond to a local dose of 0.1 mg/kg NTB. Treated animals were tested in different groups at three incrementing doses of 0.01 (i.e., 10-fold lower), 0.1 and 1 (i.e., 10-fold higher) mg/kg. Control mice were identically treated with the vehicle used for NTB-NS preparation and administration (i.e., ultrapure water).

Animal treatment This animal study was approved by the Animal Ethics Committee of the Health Sciences Centre at the Federal University of Rio de Janeiro (process no. 01200.001568/2013-87, protocol no. 157/19) and the Johns Hopkins University Animal Use and Care Committee (MO19M96). Male 10-week-old C57BL/6 mice were anesthetized with sevoflurane, and a 1-cm-long midline incision was made to expose the trachea. NTB-NS at varying doses or vehicle (i.e., ultrapure water) was intratracheally instilled into the mouse lungs using a 30-gauge needle. The cervical incision was sutured, and mice were returned to their cages.

During a period of 24 hours after the injection, the animals were observed for significant body temperature changes, weight loss, and other clinical signs of debilitation, such as piloerection, curved posture, altered respiratory rate, tearing, eyelid changes, dehydration, and reduced locomotor activity.

The influx of inflammatory cells into the airway lumen and alveolar space was quantified by counting cells recovered from BALF. Briefly, BALF was obtained 24 hours after the administration by flushing the airways two times with 1 mL of PBS and retrieving the fluid by gentle aspiration. BALF was then centrifuged (239×g, 10 minutes), and the cell pellet was resuspended in PBS. Subsequently, the cell resuspension was diluted by Türk solution, and total leukocyte population was counted on a Neubauer chamber using an optical microscope. The differential cell counting of polymorphonuclear neutrophils recovered from the BALF was conducted by staining cells using a commercial kit (Panótico Rápido L B, Pinhais, R S, Brazil), followed by calculating the percentage of neutrophils per 100 cells.

After the BALF collection, lung tissues were harvested and fixed with 4% paraformaldehyde in PBS. The tissues were embedded in paraffin blocks, cut as 4 μm-thick slices and stained with hematoxylin and eosin. The percentage of neutrophils in alveolar septa was determined by the point-counting technique, across 10 randomly selected and non-overlapping microscopic fields. Histological analyses were performed in a blinded manner.

Results

Figure 6A:
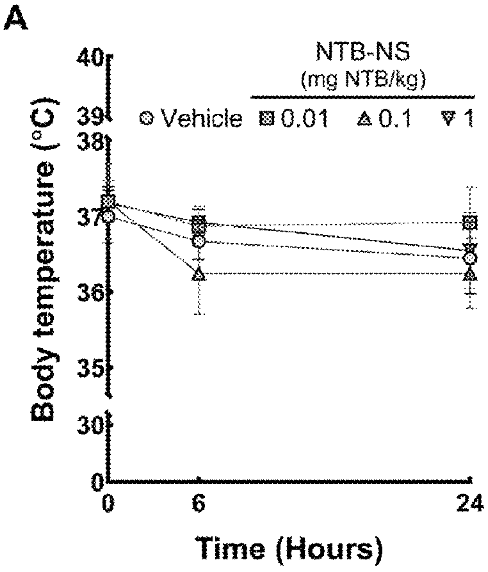
FIGS. 6A and 6B are graphs showing body temperature in healthy mice over time in 24 hours following treatment with NTB-NS at 0.01 (square) or 1 mg (inverted triangle) NTB-NS/kg (FIG. 6A) and body weight (grams) by dose: 0.01, 0.1 and 1 mg NTB-NS/kg (FIG. 6B).
Figure 6B:
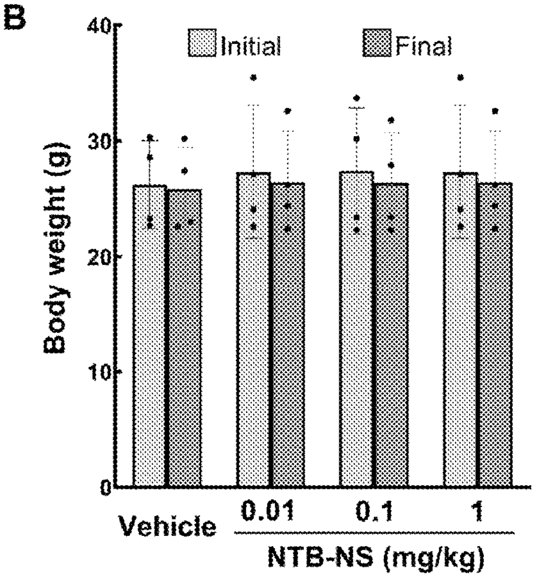

The body temperature and weight in healthy mice were unchanged 24 hours after the administration regardless of the NTB-NS dose, indicating that there was no significant acute systemic toxicity. There was no effect on body temperature (FIG. 6A) or weight (FIG. 6B).

BALF was harvested from individual animals to analyze cellularity for local safety assessment. The differences in the total number of leukocytes and percentage of neutrophils were not significant between animals that received vehicle (i.e., ultrapure water) and those that received different doses of NTB-NS. Lung tissues were harvested for histological analysis, and it was found that the percentage of neutrophils in the lung parenchyma was not elevated by intratracheal NTB-NS. This observation indicates that local administration of NTB-NS does not elicit acute adverse events in the healthy mouse lungs, presumably attributed to its preparation in an aseptic condition and to the use of the materials generally regarded as safe only (i.e., F127) for preparing the formulation.

Example 3: Evaluation of Formulation in Treatment of Fibrosis

Materials and Methods

Figure 7:
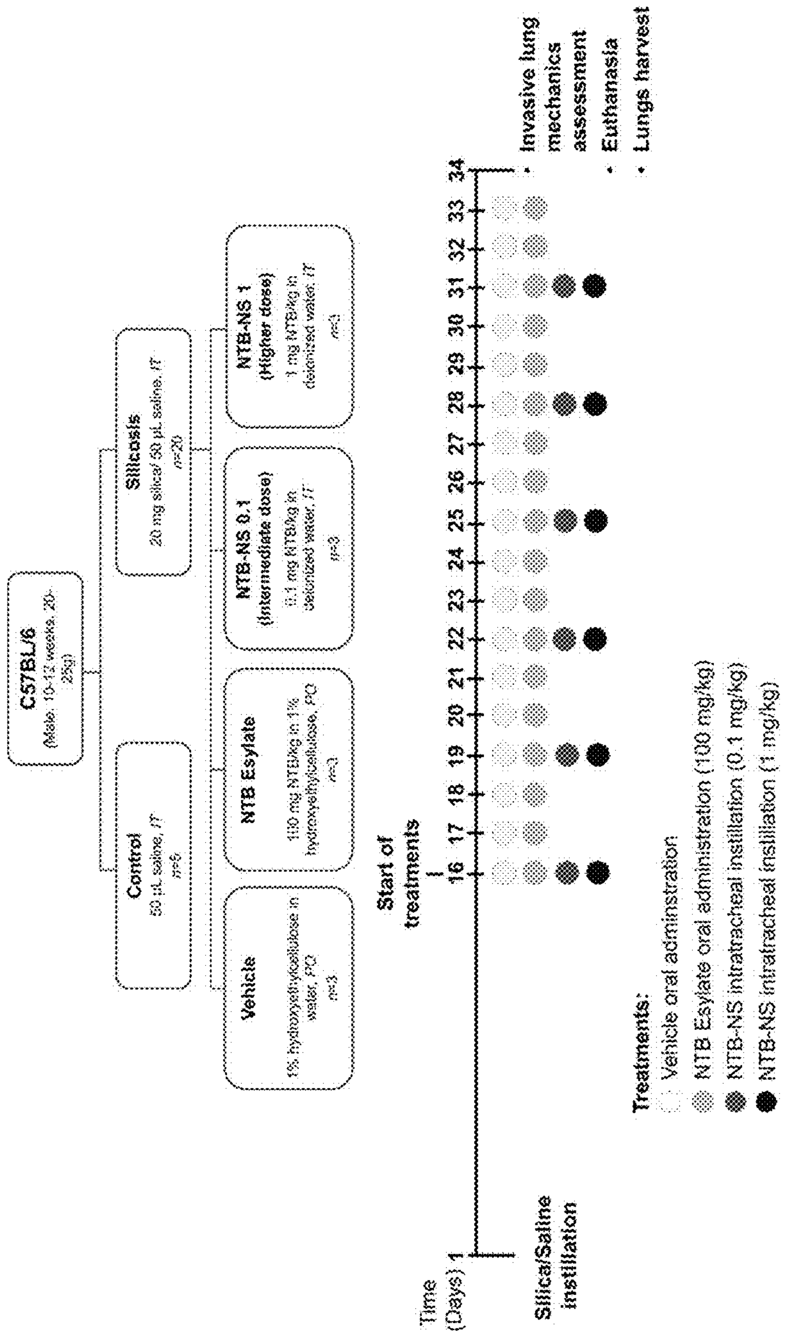
FIG. 7 is a study design for assessing the therapeutic efficacy of NTB-NS in a silica-induced pulmonary fibrosis model. The model was established by a single intratracheal instillation of silica microparticles (800 mg/kg) into the lungs of C57BL/6 mice (Silicosis); in parallel, healthy control animals received saline in an identical manner (Control). Fifteen days after the silica instillation, animals were randomly assigned to different groups to receive oral daily doses of NTB-Esy at 100 mg/kg or intratracheal NTB-NS at a NTB dose of 0.1 or 1 mg/kg every 72 hours. Lungs were harvested for analysis at Day 34. IT: intratracheal; OR: oral.

The Study design for assessing the therapeutic efficacy of NTB-NS in a preclinical silica-induced pulmonary fibrosis model is shown in FIG. 7. The silicosis model was established by a single intratracheal instillation of silica microparticles (800 mg/kg) into the lungs of C57BL/6 mice (Silicosis); in parallel, healthy control animals received saline in an identical manner (Control). Fifteen days after the silica instillation, animals were randomly assigned to different groups to receive oral daily doses of NTB-Esy at 100 mg/kg or intratracheal NTB-NS at a NTB dose of 0.1 or 1 mg/kg every 72 hours. Lungs were harvested for analysis at Day 34. IT: intratracheal; OR: oral.

Therapeutic Efficacy Assessment of NTB-NS in Preclinical Silicosis

Male 10-week-old C57BL/6 mice were randomized in a (healthy) control group and a silicosis group. To induce silicosis, silica microparticles (0.5-10 μm in particle diameter, Sigma-Aldrich) were instilled intratracheally (IT) at a dose of 800 mg/kg using a 30-gauge needle. Control group animals received saline. Fifteen days after the silica instillation, silicosis group animals were randomly redistributed in the following four experimental groups: (1) Vehicle, daily oral doses of ultrapure water (serving as an untreated control); (2) NTB-Esyte, daily oral doses of 100 mg/kg NTB (serving as a clinically-relevant control); (3) NTB-NS 0.1, IT instillation every 72 hours at 0.1 mg/kg NTB; (4) NTB-NS 1, IT instillation every 72 hours at 1 mg/kg NTB. Vehicle and NTB-Esy (LC Laboratories) solution were prepared at 1% hydroxyethyl cellulose prior to administration. Treatments were performed over a period of 18 days.

For lung mechanics analysis at the end of treatments, mice were sedated with diazepam (1 mg/kg, intraperitoneal), anesthetized with thiopenthal sodium (20 mg/kg, intraperitoneal), tracheotomized, paralyzed with vecuronium bromide (0.005 mg/kg, intravenous), and ventilated with a constant flow ventilator (Samay VR 15, Montevideo, Uruguay) using the following parameters: frequency 100 breaths/min; tidal volume 0.2 mL; fraction of inspired oxygen 0.21. The chest wall was surgically removed and a positive end-expiratory pressure of 2 cm $H_2O$ was applied. During a 10-minute ventilation period, 10 respiratory cycles using the end-inflation occlusion method were computed for evaluation of lung static elastance (Est, L). Data were analyzed using ANADAT data analysis software (RHT-InfoData Inc., Montreal Canada).

For histological analysis, left lung tissues were fixed with 4% paraformaldehyde and embedded in paraffin blocks. Blocks were cut as 4-μm thick slices and stained with Masson's trichrome to quantify collagen fiber content. The fraction areas of collagen fiber in the alveolar septa and granuloma were determined by digital densitometric recognition in ImageJ software (Image-Pro Plus 5.1 for Windows, Media Cybernetics, Silver Spring, MD). Airways and blood vessels were carefully avoided during the measurements. Lung sections were also photographed in a microscope (Leica M205 FA, Wetzlar, Germany) to quantify the fractional area occupied by granulomas. Specifically, three images of lung sections at 150-μm intervals were captured for each animal and subsequently analyzed using ImageJ to measure the areas of individual granulomas and the total lung area. The granuloma fraction was calculated as follows:

$$\text{Granuloma fraction (\%)} = \frac{\sum(\text{granulomas area})}{\text{Lung area}} \times 100$$

Evaluation of Pro-Inflammatory Responses

The influx of inflammatory cells into the airway lumen and alveolar space was quantified by counting cells recovered from BALF. Briefly, BALF was obtained 24 hours after the administration by flushing the airways two times with 1 mL of PBS and retrieving the fluid by gentle aspiration. BALF was then centrifuged (239×g, 10 minutes), and the cell pellet was resuspended in PBS. Subsequently, the cell resuspension was diluted by Türk solution, and total leukocyte population was counted on a Neubauer chamber using an optical microscope. The differential cell counting of polymorphonuclear neutrophils recovered from the BALF was conducted by staining cells using a commercial kit (Panótico Rápido LB, Pinhais, RS, Brazil), followed by calculating the percentage of neutrophils per 100 cells.

After the BALF collection, lung tissues were harvested and fixed with 4% paraformaldehyde in PBS. The tissues was embedded in paraffin blocks, cut as 4 μm-thick slices and stained with hematoxylin and eosin. The percentage of neutrophils in alveolar septa was determined by the point-counting technique, across 10 randomly selected and non-overlapping microscopic fields. Histological analyses were performed in a blinded manner.

In Vivo Therapeutic Efficacy of Locally Administered NTB-NS in the Lungs of Silicotic Animals It was next investigated whether intratracheally administered NTB-NS could attenuate the progression of silica-induced fibrosis in vivo. Treatments were commenced 15 days after the induction of silicosis by a single intratracheal instillation of silica at a dose of 800 mg/kg. Pulmonary fibrosis is established at this time point and stably retained at least up to 30 days post-instillation. Silicotic animals were treated with NTB-NS via intratracheal administration at a dose of 0.1 or 1 mg/kg every 72 hours up to 6 overall doses, while animals in a separate group received daily oral doses of NTB Esylate (NTB-Esy) at 100 mg/kg for 18 days. Daily oral treatments with NTB at 100 mg/kg significantly reduces the fibrotic score in the lungs of silicotic animals, but the model was established with a markedly lower silica dose (2.5 mg/mouse) compared to the study where individual animals were intratracheally instilled with an 8-fold greater silica dose (i.e., 20 mg/mouse).

After completing the treatment regimens, lung tissues were harvested for histopathological analysis where the fibrosis in the lung parenchyma (i.e., alveolar septa) was evaluated as an initial efficacy readout. To further evaluate the anti-fibrotic effect of locally administered NTB-NS, the level of a key pro-fibrotic mediator, TGF-β1, in the whole lung homogenates was quantified.

Next it was tested if localized treatment with NTB-NS would contribute to the normalization of the lung mechanical property, particularly the static lung elastance, based on the observation that NTB-NS effectively mitigated pulmonary fibrosis in the silicotic lungs. Elastance is a measure of the pressure required to inflate the lungs and is elevated by pulmonary fibrosis that pathologically transforms the healthy elastic tissue to a scar tissue, as observed in mouse models of silicosis.

RT-PCR

Right lung tissues were lysed for RNA extraction using the ReliaPrep RNA Miniprep System (Promega Corporation, Madison, WI) as per the manufacturer's protocol. The total RNA concentration and purity was measured by spectrophotometry using a Nanodrop ND-1000 system (Thermo Fisher Scientific, Waltham, MA).

Approximate A260/A230 and A260/A280 ratios of two were considered ideal for RNA purity. First-strand cDNA was synthesized from 1 μg purified RNA using a high-capacity cDNA reverse transcription kit (Thermo Fisher Scientific). The relative levels of mRNA were measured by SYBR Green detection (Promega) in a PCR Mastercycler Ep Realplex system (Eppendorf, Hamburg, Germany). All samples were measured in triplicate. The relative TGF-B1 transcript level was calculated as the ratio of the levels of the target gene (i.e., TGF-β1) over the control gene (i.e., acidic ribosomal phosphoprotein PO, 36B4). The primer sequences used in this study were: forward CAACCCAGCTCTGGAGAAAC (SEQ ID NO:1) and reverse GTTCTGAGCTGGCACAGTGA (SEQ ID NO:2) for 36B4; forward CTAATGGTGGACCGCAACAAC (SEQ ID NO:3) and reverse GACAGCCACTCAGGCGTATC (SEQ ID NO:4) for TGF-β1.

For statistical analysis, the normality of the data was confirmed using the Shapiro-Wilk test and the ROUT test was performed to identify outliers. One-way analysis of variance (ANOVA) followed by a Tukey post hoc test was then conducted for statistical analysis, and statistical significance was established at $P<0.05$. All tests were carried out in GraphPad Prism version 9.1.0 (GraphPad Software, San Diego, CA).

Data were analyzed using ANADAT data analysis software (RHT-InfoData Inc, Montreal Canada).

In Vivo Therapeutic Efficacy of Locally Administered NTB-NS in the Lungs of Silicotic Animals It was next investigated whether intratracheally administered NTB-NS could attenuate the progression of silica-induced fibrosis in vivo. Treatments were commenced 15 days after the induction of silicosis by a single intratracheal instillation of silica at a dose of 800 mg/kg. Pulmonary fibrosis is established at this time point and stably retained at least up to 30 days post-instillation. Silicotic animals were treated with NTB-NS via intratracheal administration at a dose of 0.1 or 1 mg/kg every 72 hours up to 6 overall doses, while animals in a separate group received daily oral doses of NTB Esylate (NTB-Esy) at 100 mg/kg for 18 days. Daily oral treatments with NTB at 100 mg/kg significantly reduces the fibrotic score in the lungs of silicotic animals, but the model was established with a markedly lower silica dose (2.5 mg/mouse) compared to the study where individual animals were intratracheally instilled with an 8-fold greater silica dose (i.e., 20 mg/mouse).

After completing the treatment regimens, lung tissues were harvested for histopathological analysis where the fibrosis in the lung parenchyma (i.e., alveolar septa) was evaluated as an initial efficacy readout. To further evaluate the anti-fibrotic effect of locally administered NTB-NS, the level of a key pro-fibrotic mediator, TGF-β1, in the whole lung homogenates was quantified.

Next it was tested if localized treatment with NTB-NS would contribute to the normalization of the lung mechanical property, particularly the static lung elastance, based on the observation that NTB-NS effectively mitigated pulmonary fibrosis in the silicotic lungs. Elastance is a measure of the pressure required to inflate the lungs and is elevated by pulmonary fibrosis that pathologically transforms the healthy elastic tissue to a scar tissue, as observed in mouse models of silicosis.

RT-PCR

Right lung tissues were lysed for RNA extraction using the RELIAPREP™ RNA Miniprep System (Promega Corporation, Madison, WI, USA) as per the manufacturer's protocol. The total RNA concentration and purity was measured by spectrophotometry using a NANODROP ND-1000 system (Thermo Fisher Scientific, Waltham, MA, USA). Approximate A260/A230 and A260/A280 ratios of two were considered ideal for RNA purity. First-strand cDNA was synthesized from 1 μg purified RNA using a high-capacity cDNA reverse transcription kit (Thermo Fisher Scientific). The relative levels of mRNA were measured by SYBR Green detection (Promega) in a PCR MASTERCYCLER EP REALPLEX system (Eppendorf, Hamburg, Germany). All samples were measured in triplicate. The relative TGF-β1 transcript level was calculated as the ratio of the levels of the target gene (i.e., TGF-β1) over the control gene (i.e., acidic ribosomal phosphoprotein PO, 36B4). The primer sequences used in this study were: forward CAACCCAGCTCTGGAGAAAC (SEQ. ID 1) e GTTCTGAGCTGGCACAGTGA for 36B4 (SEQ. ID 2); forward CTAATGGTGGACCGCAACAAC (SEQ. ID 3) and reverse GACAGCCACTCAGGCGTATC (SEQ. ID 4) for TGF-β1.

Statistical Analysis

Sample size was based on experience with models of silicosis. The normality of the data was confirmed using the Shapiro-Wilk test and the ROUT test was performed to identify outliers. One-way analysis of variance (ANOVA) followed by a Tukey post-hoc test was then conducted for statistical analysis, and statistical significance was established at $p<0.05$. All tests were carried out in GraphPad Prism version 9.1.0 (GraphPad Software, San Diego, CA, USA).

Results

It was confirmed that the silicosis model (FIG. 7) exhibited a significant elevation of static lung elastance compared to healthy control animals (control vs. silicosis-vehicle, $p<0.01$).

Figure 8A:
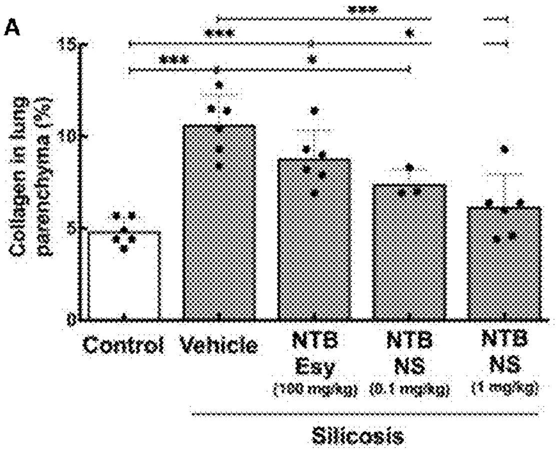
FIGS. 8A-8C are graphs showing intratracheally administered NTB-NS provides significant anti-fibrotic effect in the lungs of silicotic mice. Silicotic mice received either daily oral dose of NTB Esylate (100 mg/kg) or intratracheal NTB-NS at two different NTB doses of 0.1 or 1 mg/kg every 72 hours.

It was found that intratracheal NTB-NS given at 0.1 or 1 mg/kg NTB dose, unlike 100 mg/kg oral NTB-Esy, significantly reduced the area of collagen deposition compared to the untreated silicotic animals (silicosis-vehicle group) ($p<0.01$ or $p<0.001$, respectively) (FIG. 8A). The higher NTB-NS dose (i.e., 1 mg/kg) near-normalized the silica-induced collagen deposition in the alveolar septa.

Figure 8B:
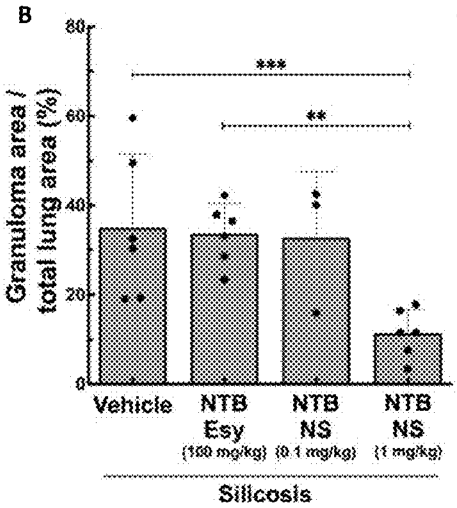
Figure 8C:
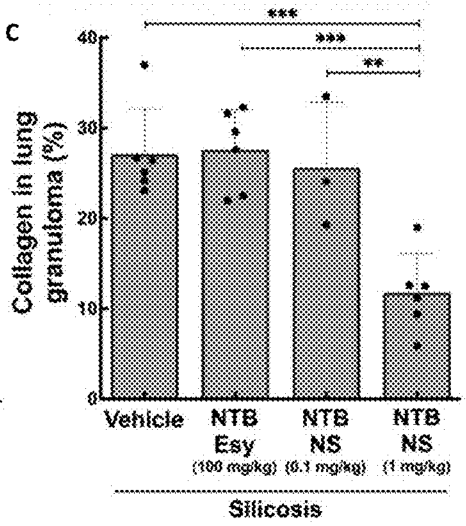

Granuloma areas, which are small inflammatory nodules widely observed in the lungs of silicotic patients, particularly those with accelerated silicosis due to very heavy silica exposure, were measured. Based on the blinded histological analysis), untreated animals and animals that received oral NTB-Esy (100 mg/kg, daily) or low-dose intratracheal NTB-NS (0.1 mg/kg, every 72 hours) similarly exhibited over 30% granuloma area on average (FIG. 8B), suggesting that these treatments were unable to alleviate the granuloma burden. In contrast, the area occupied by granuloma was markedly reduced (~10% on average) in the lungs of animals that received higher intratracheal doses (i.e., 1 mg/kg) of NTB-NS, resulting in statistically significant differences in comparison to both the untreated ($p<0.001$) and the oral dosage ($p<0.05$) groups (FIG. 8B). It was also found that intratracheal NTB-NS given at 1 mg/kg roughly halved the collagen fiber deposition within the granuloma on average in comparison to other groups (FIG. 8C). The differences were statistically significant compared to all other groups, including untreated animals ($p<0.001$) and animals treated with either oral NTB-Esy ($p<0.001$) or low-dose intratracheal NTB-NS (0.1 mg/kg) ($p<0.01$).

Figure 9A:
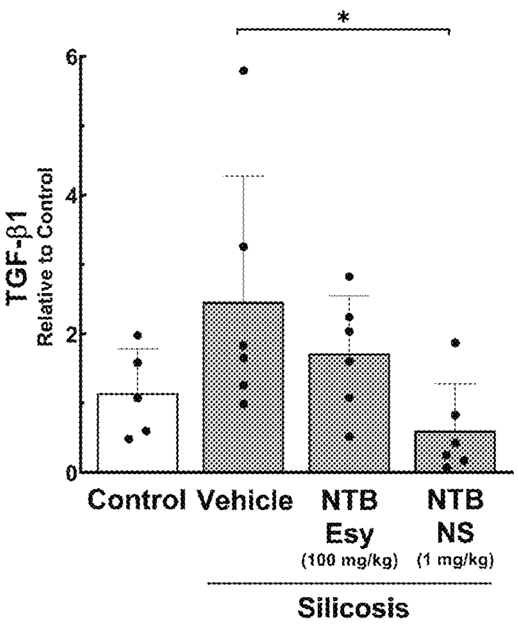
FIG. 9A is a graph of Intratracheally administered NTB-NS significantly reduces TGF-β1 expression in the lungs of silicotic mice. The TGF-β1 mRNA transcript levels in the lung tissues determined by RT-qPCR. Bars represent mean±SD (n=6 mice per group). The difference is statistically significant as indicated (*p<0.05; one-way ANOVA followed by a Tukey post-hoc test).

Upregulation of TGF-β1, induced by phagocytic uptake of inhaled crystalline silica microparticles, plays a critical role in the formation of silicotic granuloma and has been validated by post mortem examinations of lung tissues from individuals with silicosis. 0.1 mg/kg intratracheal NTB-NS dose was excluded here given its limited anti-fibrotic effect observed in the earlier study. It was found that intratracheal NTB-NS administered at 1 mg/kg every third day, but not the daily oral doses of NTB-Esy at 100 mg/kg, significantly reduced the mRNA transcript level of TGF-β1 in the lung tissues ($p<0.05$, FIG. 9A). Remarkably, the level was comparable to the homeostatic TGF-β1 transcript level observed in the lungs of healthy animals. This is in accordance with the previous in vitro observations with primary human fibroblast that NTB intervenes with TGF-β signaling and/or with associated pro-fibrotic events, including myofibroblast differentiation and collagen deposition.

Figure 9B:
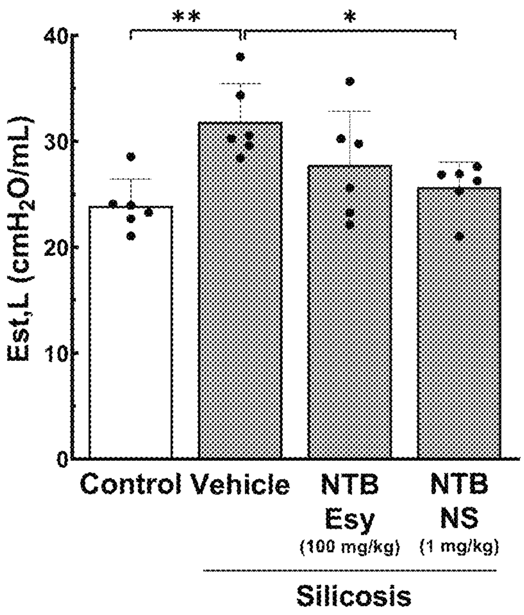
FIG. 9B is a graph of static lung elastance showing that intratracheally administered NTB-NS restores mechanical lung function of silicotic mice. Static lung elastance (Est,L). Bars represent mean±SD (n=6 mice per group). The differences are statistically significant as indicated (*p<0.05, **p<0.01; one-way ANOVA followed by a Tukey post-hoc test).

The results demonstrate that localized treatment with NTB-NS contribute to the normalization of the lung mechanical property, particularly the static lung elastance (FIG. 9B), based on our observation that NTB-NS effectively mitigated pulmonary fibrosis in the silicotic lungs. Elastance is a measure of the pressure required to inflate the lungs and is elevated by pulmonary fibrosis that pathologically transforms the healthy elastic tissue to a scar tissue, as observed in mouse models of silicosis. It was found that intratracheal NTB-NS (1 mg/kg, every third day), unlike oral NTB-Esy (100 mg/kg, daily), significantly decreased the static lung elastance ($p<0.05$) to a level on par with the healthy control animals.

The robust anti-fibrotic effects mediated by NTB-NS were achieved despite more delayed treatment onset, the lower NTB dose, and the reduced dosing frequency implemented in this study. This is attributed to sustained drug release from the NS formulation, presumably offsetting the ephemeral nature of NTB in the lung epithelium to prolong the lung residence time of the drug. Further, non-adhesive surface F127 coating enhances lung retention of the formulation by minimizing the adhesive interactions with airway mucus and lung-resident macrophages that promote the clearance of inhaled foreign matters from the lung as natural host defense mechanisms.

In summary, the NTB-NS formulation for localized pulmonary fibrosis treatment possesses characteristics to overcome key extracellular biological delivery barriers, thereby enhancing pharmacokinetic profiles of the payloads in the lung. Intratracheal NTB-NS provided remarkable anti-fibrotic activity in a mouse model of silica-induced pulmonary fibrosis without incurring local and systemic safety concerns. Importantly, the anti-fibrotic effects were attained in a therapeutic manner (i.e., treatments commenced after the disease was fully established) with a sign of functional normalization and at a 100- and a 3-fold lower dose and dosing frequency, respectively, employed for the oral dosage group that served as a clinically relevant control.

Example 4: Comparison of Telmisartan Formulation with NTB Formulation for Inhalation Treatment of Fibrosis

Materials and Methods

The NTB-NS formulation is described above.

Telmisartan (TEL) is an anti-fibrotic and blood pressure lowering drug. Particles combined with polysorbate 80 for delivery via inhalation into the lung at a dose of 0.1 mg/kg has been developed. See Chen, et al. Mol. Pharmaceutics 20(1):750-757 (2023).

Results

Figure 10A:
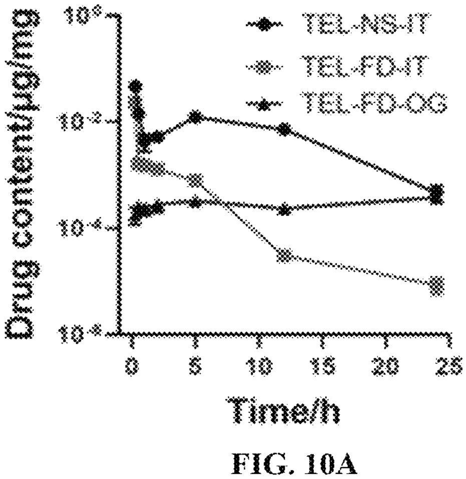
FIG. 10A-10C are graphs showing that intratracheally administered NS formulations provide marked enhanced lung PK compared to oral formulations and clinically used Polysorbate 80 may outperform PLURONIC® F127 for inhaled applications.
Figure 10B:
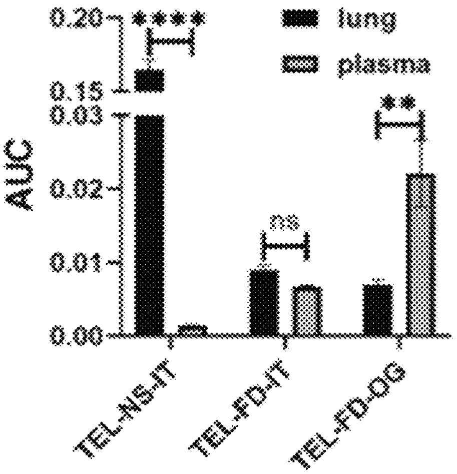
Figure 10C:
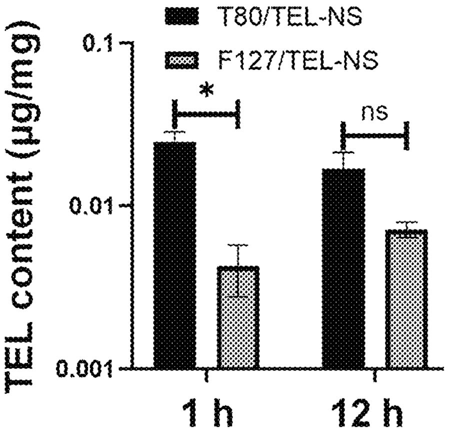

FIG. 10A-10C are graphs showing that intratracheally administered TEL-polysorbate 80 NS formulations provide marked enhanced lung PK compared to oral formulations of telmisartan and clinically used Polysorbate 80.

FIG. 10A and FIG. 10B show the PK of intratracheally administered telmisartan NS (TEL-NS coated Pluronic F127; 0.1 mg/kg) versus identically administered telmisartan free-drug (TEL-FD; 0.1 mg/kg) or orally administered TEL-FD (1 mg/kg; i.e., 10-times greater dose than inhaled).

FIG. 10C shows the lung PK of intratracheally administered TEL-NS prepared with POLYSORBATE® 80 (T80/TEL-NS) versus PLURONIC® F127 (F127/TEL-NS).

The results show the superiority of administering the drugs to the lungs as a nanoparticle suspension in combination with a surfactant.

We claim:

1. A formulation for administration to the lungs of an individual in need of treatment of pulmonary fibrosis comprising:

comprising coated nanocrystals, wherein the nancocrystals are formed of an anti-fibrotic kinase inhibitor, and the coating is formed from a non-ionic surfactant, wherein the coated nanocrystals are between 50 nm and 500 nm in diameter.

2. The formulation of claim 1 wherein the nanocrystals are formed of nintedanib.

3. The formulation of claim 1 wherein the non-ionic surfactant is selected from the group consisting of a polyoxyethylene sorbitan fatty acid ester, Polyoxyethylene 15 hydroxy stearate, Polyoxyethylene castor oil, Polyoxyethylene stearates, sorbitan fatty acid ester, Polyoxyethylene alkyl ether, or polyoxyethylene nonylphenol ether, and poloxamers.

4. The formulation of claim 3 wherein the non-ionic surfactant is a poly (oxyethylene)-poly (oxypropylene)-poly (oxyethylene) triblock copolymer or polysorbate 80.

5. The formulation of claim 1 wherein the coated nanocrystals are between 200 and 350 nm in diameter.

6. The formulation of claim 1 further comprising a cryoprotectant.

7. The formulation of claim 1 further comprising an excipient for aerosolization, intratracheal administration or inhalation administration.

8. A method of treating an individual with pulmonary fibrosis comprising administering the formulation of claim 1.

9. The method of claim 8 comprising administering the formulation as a liquid in a form for aerosolization, intratracheal administration or inhalation administration.

10. The method of claim 9 wherein the dosage is less than the oral dosage of the same inhibitor.

11. The formulation of claim 6, wherein the cryoprotectant is a disaccharide.

12. The formulation of claim 6, wherein the cryoprotectant is sucrose or trehalose.

13. The formulation of claim 6, wherein the cryoprotectant is sucrose.

14. The formulation of claim 1, further comprising a liquid carrier, wherein the coated nanocrystals are suspended in the liquid carrier.

15. The formulation of claim 14, wherein the liquid carrier is sterile water or saline.

16. A kit comprising:

(i) a formulation comprising coated nanocrystals, wherein the coated nanocrystals comprise:

(a) nanocrystals formed of an anti-fibrotic kinase inhibitor and (b) a coating formed of a non-ionic surfactant, wherein the coated nanocrystals are between 50 nm and 500 nm in diameter; and (ii) a liquid carrier, wherein the formulation and liquid carrier are packaged separately.

17. The kit of claim 16, wherein the liquid carrier is sterile water or saline.

18. The kit of claim 16, wherein the nanocrystals are formed of nintedanib.

19. The kit of claim 16, wherein the non-ionic surfactant is selected from the group consisting of a polyoxyethylene sorbitan fatty acid ester, Polyoxyethylene 15 hydroxy stearate, Polyoxyethylene castor oil, Polyoxyethylene stearates, sorbitan fatty acid ester, Polyoxyethylene alkyl ether, or polyoxyethylene nonylphenol ether, and poloxamers.

20. The kit of claim 16, wherein the non-ionic surfactant is a poly (oxyethylene)-poly (oxypropylene)-poly (oxyethylene) triblock copolymer or polysorbate 80.

* * * * *